United States Patent [19]

Teetz et al.

[11] Patent Number: 5,068,351
[45] Date of Patent: Nov. 26, 1991

[54] PROCESS FOR THE PREPARATION OF N OCTAHYDROPENTA (6) PYRROLE CARBOXYLATES

[75] Inventors: Volker Teetz, Hofheim am Taunus; Hans Wissmann, Bad Soden am Taunus; Hansjörg Urbach, Kronberg/Taunus, all of Fed. Rep. of Germany

[73] Assignee: Hoechst Aktiengesellschaft, Frankfurt am Main, Fed. Rep. of Germany

[21] Appl. No.: 560,004

[22] Filed: Jul. 27, 1990

Related U.S. Application Data

[63] Continuation of Ser. No. 403,919, Sep. 7, 1989, abandoned, which is a continuation of Ser. No. 178,767, Mar. 30, 1988, abandoned, which is a continuation of Ser. No. 943,882, Dec. 19, 1986, abandoned, which is a continuation of Ser. No. 650,715, Sep. 14, 1984, abandoned.

[30] Foreign Application Priority Data

Sep. 16, 1983 [DE] Fed. Rep. of Germany ....... 3333454

[51] Int. Cl.$^5$ .................. C07D 207/00; C07D 209/52
[52] U.S. Cl. ..................... 548/452; 530/340; 530/342; 548/253; 562/575
[58] Field of Search .................. 548/452, 253; 514/19; 562/575; 530/340, 342

[56] References Cited

U.S. PATENT DOCUMENTS 4,331,592 5/1982 Wissmann et al. .................. 548/253
4,426,325 1/1984 Wissmann et al. .................. 548/253
4,562,202 12/1985 Urbach et al. ...................... 548/253

FOREIGN PATENT DOCUMENTS

| 0018549 | 1/1980 | European Pat. Off. |
| 0012401 | 6/1980 | European Pat. Off. |
| 0012845 | 7/1980 | European Pat. Off. |
| 0037231A2 | 10/1981 | European Pat. Off. |
| 0046953 | 3/1982 | European Pat. Off. |
| 0049658 | 4/1982 | European Pat. Off. |
| 0050800 | 5/1982 | European Pat. Off. |
| 0050850A1 | 5/1982 | European Pat. Off. |
| 0090362 | 10/1983 | European Pat. Off. |
| 3322530 | 1/1985 | Fed. Rep. of Germany |
| 813034 | 4/1981 | Finland |
| 812859 | 3/1982 | Finland |
| 813283 | 4/1982 | Finland |
| 813422 | 5/1982 | Finland |
| 2491469 | 4/1982 | France |
| 64085 | 4/1981 | Israel |
| 57-77672 | 5/1982 | Japan |
| 57-112359 | 7/1982 | Japan |
| 57-91974 | 8/1982 | Japan |
| 198702 | 8/1985 | New Zealand |
| 198535 | 9/1989 | New Zealand |
| 81/5988 | 8/1982 | South Africa |
| 83/2229 | 12/1983 | South Africa |
| 2086390 | 5/1982 | United Kingdom |
| 2095682 | 10/1982 | United Kingdom |

OTHER PUBLICATIONS

Leonard et al., J. Am. Chem. Soc., 77, 439 (1955).
Leonard et al., J. Am. Chem. Soc., 78, 3457 (1956).
Leonard et al., J. Am. Chem. Soc., 78, 3463 (1956).
Leonard et al., J. Am. Chem. Soc., 81, 5627 (1959).
Koelsch et al., J. Org. Chem., 26, 1104 (1961).
Griot et al., Helv. Chim. Acta, 42, 121 (1959).
Bonnett et al., J. Chem. Soc., 2807 (1959).
Battersby et al., J. Chem. Soc., 4333 (1958).
Rosenblatt et al., The Chemistry of Functional Groups, Supplement F: The Chemistry of Amino, Nitroso and Nitro Compounds and Their Derivatives, Part II, S. Patai, ed., Wiley & Sons: New York 1982, pp. 1100–1104.
L. W. Haynes, Enamines, A. G. Cook, ed., Marcel Decker, Inc.: 1969, pp. 68–79, 261–269, 413.
Fieser & Fieser, Reagents for Organic Synthesis, vol. 1, pp. 644–651 (1967).
Boehme et al., Iminium Salts in Organic Chemistry, Part I (E. C. Taylor, ed.), Wiley & Sons: New York, 1976, p. 143.
S. Dayagi et al., The Chemistry of Functional Groups, The Chemistry of The Carbon–Nitrogen Double Bond, S. Patai, ed., Wiley & Sons: New York, 1970, p. 119.
W. Greenlee et al., J. Med. Chem., 28, 434–442 (1985).
K. Ogawa et al., J. Chem. Soc., Perkin Trans. I, 3031–3035 (1982).

(List continued on next page.)

*Primary Examiner*—Lester L. Lee
*Attorney, Agent, or Firm*—Finnegan, Henderson, Farabow, Garrett & Dunner

[57] ABSTRACT

The invention relates to a process for the preparation of compounds of the formula I

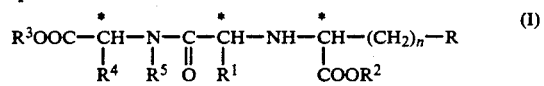

in which n is 1 or 2, R denotes hydrogen or an organic radical, $R^1$ denotes an organic radical, $R^2$ and $R^3$ are identical or different and denote hydrogen or an organic radical, and $R^4$ and $R^5$, together with the atoms bearing them, form a monocyclic, bicyclic or tricyclic heterocyclic ring system having 5 to 15 carbon atoms, which process comprises reacting compounds of the formula II defined in the description with compounds of the formula IV defined in the description, in the presence of phosphinic anhydrides of the formula III, where appropriate eliminating radicals which have been introduced to protect other functional groups and, where appropriate, esterifying free carboxyl groups in a manner known per se.

18 Claims, No Drawings

OTHER PUBLICATIONS

R. Bacon and D. Stewart, J. Chem. Soc. (C), 1384–1387 (1966).

R. Bacon et al., J. Chem. Soc. (C), 1388–1389 (1966).

Patchett et al., Nature, 288, 280–283 (1980).

Booth et al., Chemistry and Industry, 466–467 (1956).

Booth et al., J. Chem. Soc., Part I, 1050–1054 (1959).

Murakoshi et al., Chemical Abstracts, 61, 9465(e) (1964).

Cushman et al., Fed. Proc., 38 (13), 2778–2782 (1979).

Houben-Weyl, Methoden der Organischen Chemie, 7(2b), 1403–1404 (1976).

Katritskaya, Dzh. Lagorskaya Khimia Geterosikl. Soedin., Moskow 1963, pp. 155–158.

Anderson, Jr. et al., J. Org. Chem., 43(1), 54–57 (1978).

Bertho et al., "Synthesen In Der 2-Azabicyclo[0.3.-3]-octan-Reihe", Chemische Berichte, 92(7), 2218–2235 (1959).

Farkas et al., J. Org. Chem., 22, 1261–1263 (1957).

Taylor et al., J. Org. Chem., 38(16), 2817–2821 (1973).

Taylor et al., Heterocycles, 25, 343–345 (1987).

English language translation of Mitzlaff et al., Liebig's Ann. Chem., 1713–1733 (1978).

Chem. Berichte 86: 1524–1528 (1953).

Quarterly Reviews 25: 323–341 (1971).

Chem. Abst. 49/1955/3009c.

PROCESS FOR THE PREPARATION OF N OCTAHYDROPENTA (6) PYRROLE CARBOXYLATES

This application is a continuation of application Ser. No. 07/403,919, filed Sept. 7, 1989 and now abandoned, which is a continuation of application Ser. No. 07/178,767, filed Mar. 30, 1988, and now abandoned which is a continuation of application Ser. No. 06/943,822 filed Dec. 19, 1986 and now abandoned which is a continuation of application Ser. No. 06/650,715 filed Sept. 1, 1984, and now abandoned.

The invention relates to a process for the preparation of compounds of the formula I

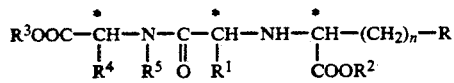
(I)

in which n is 1 or 2, R denotes hydrogen, an optionally substituted aliphatic radical having 1 to 8 carbon atoms, an optionally substituted alicyclic radical having 3–9 carbon atoms, an optionally substituted aromatic radical having 6–12 carbon atoms, an optionally substituted araliphatic radical having 7–14 carbon atoms, an optionally substituted alicyclic-aliphatic radical having 7–14 carbon atoms, or a radical $OR^a$ or $SR^a$, in which $R^a$ represents an optionally substituted aliphatic radical having 1–4 carbon atoms, an optionally substituted aromatic radical having 6–12 carbon atoms or an optionally substituted heteroaromatic radical having 5–12 ring atoms, $R^1$ denotes hydrogen, an optionally substituted aliphatic radical having 1 to 6 carbon atoms, an optionally substituted alicyclic radical having 3–9 carbon atoms, an optionally substituted alicyclic-aliphatic radical having 4–13 carbon atoms, an optionally substituted aromatic radical having 6–12 carbon atoms, an optionally substituted araliphatic radical having 7–16 carbon atoms, an optionally substituted heteroaromatic radical having 5–12 ring atoms, or the side chain, protected when necessary, of a naturally occurring α-amino acid, $R^2$ and $R^3$ are identical or different and denote hydrogen, an optionally substituted aliphatic radical having 1–6 carbon atoms, an optionally substituted alicyclic radical having 3–9 carbon atoms, an optionally substituted aromatic radical having 6–12 carbon atoms, or an optionally substituted araliphatic radical having 7–16 carbon atoms, and $R^4$ and $R^5$, together with the atoms bearing them, form a monocyclic, bicyclic or tricyclic heterocyclic ring system having 5 to 15 carbon atoms, which process comprises reacting compounds of the formula II

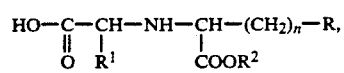
(II)

in which n, R, $R^1$ and $R^2$ have the meanings defined above, in the presence of phosphinic anhydrides of the formula III

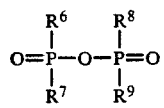
(III)

in which $R^6$, $R^7$, $R^8$ and $R^9$ are identical or different and represent alkyl and/or aralkyl, with compounds of the formula IV

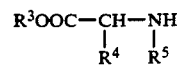
(IV)

in which $R^3$, $R^4$ and $R^5$ have the meanings defined above, where appropriate eliminating radicals which have been introduced to protect other functional groups and, where appropriate, esterifying free carboxyl groups in a manner known per se.

Particularly suitable ring systems of these types are those from the following group:

Pyrrolidine (A); piperidine (B); tetrahydroisoquinoline (C); decahydroisoquinoline (D); octahydroindole (E); octahydrocyclopenta[b]pyrrole (F); 2-azabicyclo[2.2.2]-octane (G); 2-azabicyclo[2.2.1]heptane (H); 2-azaspiro[4.5]decane (I); 2-azaspiro[4.4]nonane (J); spiro[(bicyclo 2.2.1 heptane)-2,3-pyrrolidine (K); spiro(-bicyclo[2.2.2]octane)-2,3-pyrrolidine] (L); 2-azatricyclo[4.3.0.1^{6,9}]-decane (M); decahydrocyclohepta[b]pyrrole (N); octahydroisoindole (O); octahydrocyclopenta[c]pyrrole (P); 2,3,3a,4,5,7a-hexahydroindole (Q); tetrahydrothiazole (R); 2-azabicyclo[3.1.0]hexane (S); all of which can be substituted where appropriate. However, the unsubstituted systems are preferred.

The suitable cyclic amino acid esters have the following structural formulae.

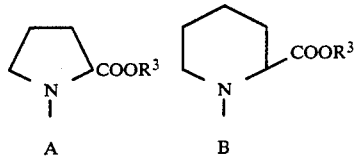

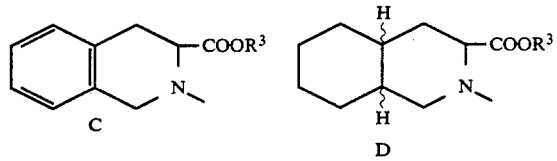

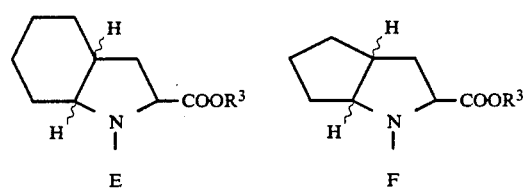

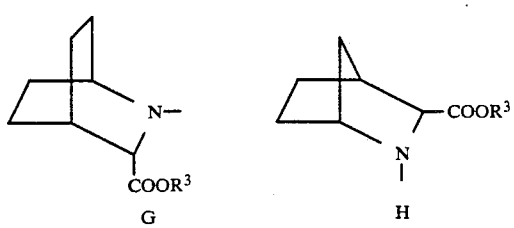

-continued

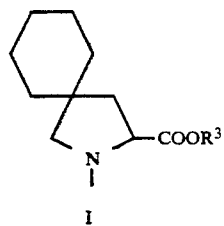

I

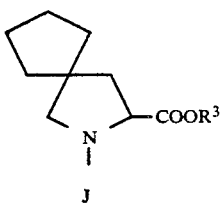

J

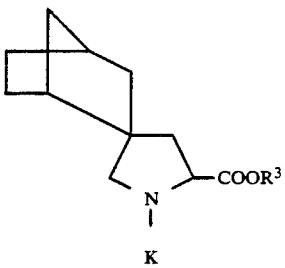

K

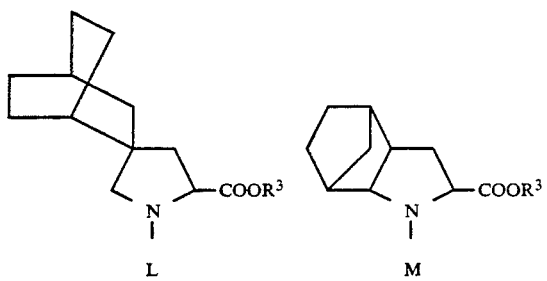

L     M

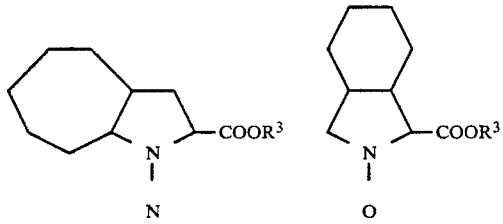

N     O

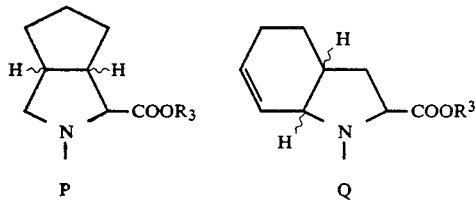

P     Q

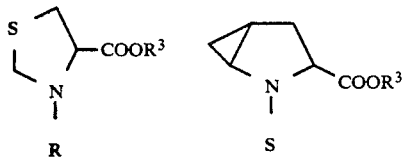

R     S

A large number of processes is known for the preparation of carboxamide and peptide bonds (see, for example, Houben-Weyl, Methoden der Organischen Chemie (Methods of Organic Chemistry), vol. XV, part II, pages 1–364, and Angew. Chemie 92, 129 (1980)). All these processes aim, with variable success, at fulfilling the criteria necessary for the synthesis of peptides, namely of freedom from racemisation, of straightforward and mild procedures giving high yields and of readily accessible starting materials which are, as far as possible, nonhazardous.

A process for the preparation of compounds containing carboxamide groups by reacting compounds containing COOH groups with compounds which contain a free NH$_2$ group, in the presence of dialkylphosphinic anhydrides, is known from European Patent A 56,618.

The yields in the methods known to date for the preparation of compounds of the formula I from compounds of the formula II and IV (for example the HOBt-DCCI method using DMF or acetonitrile as solvents) are 50–75%. In the case of DCCI, there are difficulties associated with completely removing the dicyclohexylurea which is produced, in addition severe allergies to carbodiimides are known. Other reagents, for example other anhydrides of phosphorus acids, are suitable in principle to replace the HOBt process, but the object is to avoid using reactive reagents in order to avert side reactions (for example with the unprotected secondary amino group in the compound of the formula II).

The present process represents a new way of using the above-mentioned conditions for an economic synthesis of compounds of the formula I. By means of the process according to the invention compounds of the formula II can be reacted with those of the formula IV under mild conditions to give compounds of the formula I in good yields. It is a surprise that the process does not involve the occurrence of side reactions on the unprotected secondary amino group in the compounds of the formula II or the final product.

The radicals introduced to protect the functional groups are subsequently eliminated in a customary manner.

Those phosphinic anhydrides of the formula III in which $R^6$ to $R^9$ represent ($C_1$ to $C_{10}$)-alkyl and/or ($C_7$–$C_{10}$)-aralkyl (for example benzyl) are preferred. Moreover, anhydrides in which both P atoms have the same substituents are preferred.

Within the scope of the invention, anhydrides of the formula III in which $R^6$ to $R^9$ is each lower alkyl, preferably one having 1 to 4 carbon atoms, are particularly suitable.

The phosphinic anhydrides used according to the invention are colorless liquids. They are stable at room temperature and can be distilled under reduced pressure without decomposition. They are soluble ($C_1$–$C_3$-alkyl compounds) in most solvents, in particular in lipid solvents, such as chloroform or methylene chloride, but also in polar solvents, such as DMF, DMA and water. Decomposition takes place slowly in water.

Examples of anhydrides of dialkylphosphinic acids which may be mentioned are: methylpropylphosphinic anhydride, methylbutylphosphinic anhydride, diethylphosphinic anhydride, di-n-propylphosphinic anhydride, and di-n-butylphosphinic anhydride, in particular methylethylphosphinic anhydride.

The dialkylphosphinic anhydrides can be prepared in a manner known per se, for example by reacting the dialkylphosphinyl chlorides with alkyl dialkylphosphinates at 150°–160° C. (Houben-Weyl, Methoden der Organischen Chemie, published by G. Thieme, Stuttgart, 1963, vol. XII, pages 266 et seq.). Processes in which dialkylphosphinic acids, their salts or their esters are reacted with phosgene are particularly preferred (German Patent 2,129,583 and German Offenlegungsschrift 2,225,545).

A preferred embodiment comprises preparing compounds of the formula I in which n is 1 or 2, R denotes hydrogen, alkyl having 1-8 carbon atoms, alkenyl having 2-6 carbon atoms, cycloalkyl having 3-9 carbon atoms, aryl having 6-12 carbon atoms, which can be monosubstituted, disubstituted or trisubstituted by ($C_1$-$C_4$)-alkyl, ($C_1$-$C_4$)-alkoxy, hydroxyl, halogen, nitro, amino, aminomethyl, ($C_1$-$C_4$)-alkylamino, ($C_1$-$C_4$)-acylamino, preferably ($C_1$-$C_4$)-alkanoylamino, methylenedioxy, carboxyl, cyano and/or sulfamoyl, alkoxy having 1-4 carbon atoms, aryloxy having 6-12 carbon atoms, which can be substituted as described above for aryl, monocyclic or bicyclic heteroaryloxy having 5-7 or 8-10 ring atoms respectively, 1 or 2 of these ring atoms being sulfur or oxygen atoms and/or 1 to 4 ring atoms being nitrogen, which can be substituted as described above for aryl, amino-($C_1$-$C_4$)-alkyl, ($C_1$-$C_4$)-alkanoylamino-($C_1$-$C_4$)-alkyl, ($C_7$-$C_{13}$)-aroylamino-($C_1$-$C_4$)-alkyl, ($C_1$-$C_4$)-alkoxycarbonylamino-($C_1$-$C_4$)-alkyl, ($C_6$-$C_{12}$)-aryl-($C_1$-$C_4$)-alkoxycarbonylamino-($C_1$-$C_4$)-alkyl, ($C_6$-$C_{12}$)-aryl-($C_1$-$C_4$)-alkylamino-($C_1$-$C_4$)-alkyl, ($C_1$-$C_4$)-alkylamino-($C_1$-$C_4$)-alkyl, di-($C_1$-$C_4$)-alkylamino ($C_1$-$C_4$)-alkyl, guanidino-($C_1$-$C_4$)-alkyl, imidazolyl, indolyl, ($C_1$-$C_4$)-alkylthio, ($C_1$-$C_4$)-alkylthio-($C_1$-$C_4$)-alkyl, ($C_6$-$C_{12}$)-arylthio-($C_1$-$C_4$)-alkyl, which can be substituted in the aryl moiety as described above for aryl, ($C_6$-$C_{12}$)-aryl-($C_1$-$C_4$)-alkylthio, which can be substituted in the aryl moiety as described above for aryl, carboxy-($C_1$-$C_4$)-alkyl, carboxyl, carbamoyl, carbamoyl-($C_1$-$C_4$)-alkyl, ($C_1$-$C_4$)-alkoxycarbonyl-($C_1$-$C_4$)-alkyl, ($C_6$-$C_{12}$)-aryloxy-($C_1$-$C_4$)-alkyl, which can be substituted in the aryl moiety as described above for aryl, or ($C_6$-$C_{12}$)-aryl-($C_1$-$C_4$)-alkoxy, which can be substituted in the aryl moiety as described above for aryl, $R^1$ denotes hydrogen, alkyl having 1-6 carbon atoms, alkenyl having 2-6 carbon atoms, alkynyl having 2-6 carbon atoms, cycloalkyl having 3-9 carbon atoms, cycloalkenyl having 5-9 carbon atoms, ($C_3$-$C_9$)-cycloalkyl-($C_1$-$C_4$)-alkyl, ($C_5$-$C_9$)-cycloalkenyl-($C_1$-$C_4$)-alkyl, optionally partially hydrogenated aryl having 6-12 carbon atoms, which can be substituted as described above for R, ($C_6$-$C_{12}$)-aryl-($C_1$-$C_4$)-alkyl or ($C_7$-$C_{13}$)-aroyl-($C_1$ or $C_2$)-alkyl, both of which can be substituted as the previous aryl, monocyclic or bicyclic, optionally partially hydrogenated, heteroaryl having 5-7 or 8-10 ring atoms respectively, 1 or 2 of these ring atoms being sulfur or oxygen atoms and/or 1 to 4 ring atoms being nitrogen atoms, which can be substituted as the previous aryl, or the optionally protected side chain of a naturally occurring α-amino acid $R^1$—CH(NH$_2$)—COOH, $R^2$ and $R^3$ are identical or different and denote hydrogen, alkyl having 1-6 carbon atoms, alkenyl having 2-6 carbon atoms, di-($C_1$-$C_4$)-alkylamino-($C_1$-$C_4$)-alkyl, ($C_1$-$C_5$)-alkanoyloxy-($C_1$-$C_4$)-alkyl, ($C_1$-$C_6$)-alkoxycarbonyloxy-($C_1$-$C_4$)-alkyl, ($C_7$-$C_{13}$)-aroyloxy-($C_1$-$C_4$)-alkyl, ($C_6$-$C_{12}$)-aryloxycarbonyloxy-($C_1$-$C_4$)-alkyl, aryl having 6-12 carbon atoms, ($C_6$-$C_{12}$)-aryl-($C_1$-$C_4$)-alkyl, ($C_3$-$C_9$)-cycloalkyl or ($C_3$-$C_9$)-cycloalkyl-($C_1$-$C_4$)-alkyl, and $R^4$ and $R^5$ have the above-mentioned meaning, during the reaction the free amino, alkylamino, hydroxyl, carboxyl, mercapto and/or guanidino groups present, where appropriate, in the radicals R to $R^5$ being protected in a manner known per se (cf. for example Kontakte Merck 3/79, pages 14 et seq. and 1/80, pages 23 et seq.).

A particularly preferred embodiment comprises preparing compounds of the formula I in which n is 1 or 2, R denotes ($C_1$ to $C_6$)-alkyl, ($C_2$ to $C_6$)-alkenyl, ($C_3$ to $C_9$)-cycloalkyl, amino-($C_1$-$C_4$)-alkyl, ($C_2$-$C_5$)-acylamino-($C_1$-$C_4$)-alkyl, ($C_7$-$C_{13}$)-aroylamino-($C_1$-$C_4$)-alkyl, ($C_1$-$C_4$)-alkoxycarbonylamino-($C_1$-$C_4$)-alkyl, ($C_6$ to $C_{12}$)-aryl-($C_1$-$C_4$)-alkoxycarbonylamino-($C_1$-$C_4$)-alkyl, ($C_6$ to $C_{12}$)-aryl, which can be monosubstituted, disubstituted or trisubstituted by ($C_1$ to $C_4$)-alkyl, ($C_1$ to $C_4$)-alkoxy, hydroxyl, halogen, nitro, amino, ($C_1$ to $C_4$)-alkylamino, di-($C_1$ to $C_4$)-alkylamino and/or methylenedioxy, or 3-indolyl, in particular methyl, ethyl, cyclohexyl, tert.-butoxycarbonylamino-($C_1$-$C_4$)-alkyl, benzoyloxycarbonylamino-($C_1$-$C_4$)-alkyl or phenyl, which can be monosubstituted or disubstituted or, in the case of methoxy, trisubstituted by phenyl, ($C_1$ or $C_2$)-alkyl, ($C_1$ or $C_2$)-alkoxy, hydroxyl, fluorine, chlorine, bromine, amino ($C_1$ to $C_4$)-alkylamino, di-($C_1$ to $C_4$)-alkylamino, nitro and/or methylenedioxy, $R^1$ denotes hydrogen or ($C_1$ to $C_6$)-alkyl, which can optionally be substituted by amino, ($C_1$ to $C_6$)-acylamino or benzoylamino, ($C_2$ to $C_6$)-alkenyl, ($C_3$ to $C_9$)-cycloalkyl, ($C_5$ to $C_9$)-cycloalkenyl, ($C_3$ to $C_7$)-cycloalkyl-($C_1$ to $C_4$)-alkyl, ($C_6$ to $C_{12}$)-aryl or partially hydrogenated aryl, each of which can be substituted by ($C_1$ to $C_4$)-alkyl, ($C_1$ or $C_2$)-alkoxy or halogen, ($C_6$-$C_{12}$)-aryl-($C_1$ to $C_4$)-alkyl or ($C_7$-$C_{13}$)-aroyl-($C_1$-$C_2$)-alkyl, both of which can be substituted in the aroyl moiety as defined previously, a monocyclic or bicyclic heterocyclic radical having 5 to 7 or 8 to 10 ring atoms respectively, 1 to 2 of these ring atoms being sulfur or oxygen atoms and/or 1 to 4 ring atoms being nitrogen atoms, or a side chain of a naturally occurring, optionally protected, α-amino acid, but particularly denotes hydrogen, ($C_1$ to $C_3$)-alkyl, ($C_2$ or $C_3$)-alkenyl, the optionally protected side chain of lysine, benzyl, 4-methoxybenzyl, 4-ethoxybenzyl, phenethyl, 4-aminobutyl or benzoylmethyl, $R^2$ and $R^3$, being identical or different radicals, denote hydrogen, ($C_1$ to $C_6$)-alkyl, ($C_2$ to $C_6$)-alkenyl or ($C_6$ to $C_{12}$) aryl-($C_1$ to $C_4$)-alkyl, but in particular denote hydrogen, ($C_1$ to $C_4$)-alkyl or benzyl, and $R^4$ and $R^5$ have the above-mentioned meaning, during the reaction other functional groups being protected as described above.

An example of a particularly preferred process leads to compounds of the formula I in which n is 2, R denotes phenyl, $R^1$ denotes methyl, $R^2$ and $R^3$ denote identical or different ($C_1$ to $C_6$)-alkyl radicals or ($C_7$ to $C_{10}$)-aralkyl radicals (such as benzyl or nitrobenzyl), and $R^4$ and $R^5$ together represent a radical of the formula

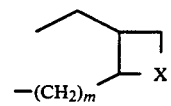

in which m denotes 0 or 1, and X denotes a bond, —CH$_2$—CH$_2$—, —CH$_2$—CH$_2$—CH$_2$— or —CH=CH—CH$_2$—, it also being possible for a 6-membered ring formed with X to be a benzene ring.

In this context and in the following, aryl is to be understood preferably to include optionally substituted phenyl, biphenylyl or naphthyl. A corresponding statement applies to radicals derived from aryl, such as aryloxy, and arylthio. Aroyl is particularly understood to include benzoyl. Aliphatic radicals can be straight-chain or branched.

Examples of a monocyclic or bicyclic heterocyclic radical having 5 to 7 or 8 to 10 ring atoms respectively, 1 or 2 of these ring atoms being sulfur or oxygen atoms and/or 1 to 4 of these ring atoms being nitrogen atoms, are understood to include thienyl, benzo[b]thienyl, furyl, pyranyl, benzofuryl, pyrrolyl, imidazolyl, pyrazolyl, pyridyl, pyrimidinyl, pyridazinyl, indazolyl, isoindolyl, indolyl, purinyl, quinolizinyl, isoquinolinyl, phthalazinyl, naphthyridinyl, quinoxalinyl, quinazolyl, cinnolinyl, pteridinyl, oxazolyl, isoxazolyl, thiazolyl or isothiazolyl. It is also possible for these radicals to be partially or completely hydrogenated.

Naturally occurring α-amino acids are described in, for example, Houben-Weyl, Methoden der Organischen Chemie, vol. XV/1 and XV/2.

Where $R^1$ represents a side chain of a protected naturally occurring α-amino acid, such as, for example, protected Ser, Thr, Asp, Asn, Glu, Gln, Arg, Lys, Hyl, Cys, Orn, Cit, Tyr, Trp, His or Hyp, the protective groups preferred are those customary in peptide chemistry (cf. Houben-Weyl, vol. XV/1 and XV/2). Where $R^1$ denotes the protective side chain of lysine, the known amino protective groups, but particularly Z, Boc or ($C_1$–$C_6$)-alkanoyl are preferred. Suitable and preferred as O-protective groups for tyrosine are ($C_1$–$C_6$)-alkyl, in particular methyl or ethyl.

Using the process according to the invention, depending on which chiral starting compounds have been used, compounds of the formula I in which the centers of chirality have the S and/or R configuration, or which exist as racemates, are obtained.

The following compounds can be obtained particularly advantageously using the process according to the invention.

N-(1-S-carboethoxy-3-phenylpropyl)-S-alanyl-S-proline benzyl ester
N-(1-R-carboethoxy-3-phenylpropyl)-S-alanyl-S-proline benzyl ester
N-(1-R,S-carboethoxy-3-phenyl-propyl)-S-alanyl-S-proline benzyl ester
N-(1-S-carboethoxy-3-cyclohexylpropyl)-S-alanyl-S-proline benzyl ester
N-(1-R-carboethoxy-3-cyclohexylpropyl)-S-alanyl-S-proline benzyl ester
N-(1-R,S-carboethoxy-3-cyclohexylpropyl)-S-alanyl-S-proline benzyl ester
N-(1-S-carboethoxy-3-phenyl-propyl)-N$_\epsilon$-benzyloxycarbonyl-S-[ysyl-S-proline tert.-butyl ester
N-(1-S-carboethoxy-3-phenylpropyl)-S-tyrosyl-S-proline benzyl ester
N-(1-S-carboethoxy-3phenyl-propyl)-O-methyl-S-tyrosyl-S-proline benzyl ester
N-(1-S-carboethoxy-3-phenylpropyl)-O-ethyl-S-tyrosyl-S-proline benzyl ester
Benzyl N-(1-S-carboethoxy-3-phenylpropyl)-S-alanyl-S-pipecolate
Benzyl N-(1-S-carboethoxy-3-cyclohexylpropyl)-S-alanyl-S-pipecolate
Tert.-butyl N-(1-S-carboethoxy-3-phenylpropyl)-S-alanyl-S-1,2,3,4-tetrahydroisoquinoline-3-carboxylate
Tert.-butyl N-(1-S-carboethoxy-3-cyclohexylpropyl)-S-alanyl-S-1,2,3,4-tetrahydroisoquinoline-3-carboxylate
Tert.-butyl N-(1-S-carboethoxy-3-phenylpropyl)-N$_\epsilon$-benzylcarbonyl-S-lysyl-S-1,2,3,4-tetrahydroisoquinoline-3-carboxylate
Tert.-butyl N-(1-S-carboethoxy-3-phenylpropyl)-O-ethyl-S-tyrosyl-S-1,2,3,4-tetrahydroisoquinoline-3-carboxylate
Benzyl N-(1-S-carboethoxy-3-phenylpropyl)-S-alanyl-3S-decahydroisoquinoline-3-carboxylate
Benzyl N-(1-S-carboethoxy-3-phenylpropyl)-S-alanyl-(2S,3aS,7aS)-octahydroindole-2-carboxylate
Benzyl N-(1-S-carboethoxy-3-cyclohexylpropyl)-S-alanyl-(2S,3aS,7aS)-octahydroindole-2-carboxylate
Tert.-butyl N-(1-S-carboethoxy-3-phenylpropyl)-N$_\epsilon$-benzyloxycarbonyl-S-lysyl-(2S,3aS,7aS)-octahydroindole-2-carboxylate
Tert.-butyl N-(1-S-carboethoxy-3-cyclohexylpropyl)-N$_\epsilon$-benzyloxycarbonyl-S-lysyl-(2S,3aS,7aS)-octahydroindole-2-carboxylate
Benzyl N-(1-S-carboethoxy-3-phenylpropyl)-O-methyl-S-tyrosyl-(2S,3aS,7aS)-octahydroindole-2-carboxylate
Benzyl N-(1-S-carboethoxy-3-phenylpropyl)-O-ethyl-S-tyrosyl-(2S,3aS,7aS)-octahydroindole-2-carboxylate
Benzyl N-(1-S-carboethoxy-4,4-dimethylphenyl)-O-alanyl-(2S,3aS,7aS)-octahydroindole-2-carboxylate
Benzyl N-[1-S-carboethoxy-3-(4-fluorophenyl)propyl]-S-alanyl-(2S,3aS,7aS)-octahydroindole-2-carboxylate
Benzyl N-[1-S-carboethoxy-3-(4-methoxyphenyl)propyl]-S-alanyl-(2S,3aS,7aS)-octahydroindole-2-carboxylate
Benzyl N-[1-S-carboethoxy-3-(3,4-dimethoxyphenyl)propyl]-S-alanyl-(2S,3aS,7aS)-octahydroindole-2-carboxylate
Benzyl N-(1-S-carboethoxy-3-cyclopentylpropyl)-S-alanyl-(2S,3aS,7aS)-octahydroindole-2-carboxylate
Benzyl N-(1-S-carboethoxy-3-phenylpropyl)-S-alanyl-(2S,3aR,7aS)-octahydroindole-2-carboxylate
Benzyl N-(1-S-carboethoxy-3-cyclohexylpropyl)-S-alanyl-(2S,3aR,7aS)-octahydroindole-2-carboxylate
Tert.-butyl N-(1-S-carboethoxy-3-phenylpropyl)-N$_\epsilon$-benzyloxycarbonyl-S-lysyl-(2S,3aR,7aS)-octahydroindole-2-carboxylate
Benzyl N-(1-S-carboethoxy-3-cyclohexylpropyl)-N$_\epsilon$-benzyloxycarbonyl-S-lysyl-(2S,3aR,7aS)-octahydroindole-2-carboxylate
Benzyl N-(1-S-carboethoxy-3-phenylpropyl)-O-ethyl-S-tyrosyl-(2S,3aR,7aS)-octahydroindole-2-carboxylate
Benzyl N-(1-S-carboethoxy-3-phenylpropyl)-S-alanyl-(2S,3aR,7aR)-octahydroindole-2-carboxylate
Tert.-butyl N-(1-S-carboethoxy-3-phenylpropyl)-N$_\epsilon$-benzyloxycarbonyl-S-lysyl-(2S,3aR,7aR)-octahydroindole-2-carboxylate
Benzyl N-(1-S-carboethoxy-3-cyclohexylpropyl)-S-alanyl-(2S,3aR,7aR)-octahydroindole-2-carboxylate
Benzyl N-(1-S-carboethoxy-3-cyclohexylpropyl)-O-ethyl-S-tyrosyl-(2S,3aR,7aR)-octahydroindole-2-carboxylate
Benzyl N-(1-S-carboethoxy-3-phenylpropyl)-S-alanyl-(2S,3aS,7aR)-octahydroindole-2-carboxylate
Benzyl N-(1-S-carboethoxy-3-phenylpropyl)-O-ethyl-S-tyrosyl-(2S,3aS,7aS)-octahydroindole-2-carboxylate
Benzyl N-(1-S-carboethoxy-4,4-dimethylphenyl)-O-alanyl-(2S,3aS,7aS)-octahydroindole-2-carboxylate
Benzyl N-[1-S-carboethoxy-3-(4-fluorophenyl)propyl]-S-alanyl-(2S,3aS,7aS)-octahydroindole-2-carboxylate
Benzyl N-[1-S-carboethoxy-3-(4-methoxyphenyl)propyl]-S-alanyl-(2S,3aS,7aS)-octahydroindole-2-carboxylate
Benzyl N-[1-S-carboethoxy-3-(3,4-dimethoxyphenyl)propyl]-S-alanyl-(2S,3aS,7aS)-octahydroindole-2-carboxylate Benzyl N-(1-S-carboethoxy-3-cyclopentylpropyl)-S-alanyl-(2S,3aS,7aS)-octahydroindole-2-carboxylate Tert.-butyl N-(1-S-carboethoxy-3-phenylpropyl)-N$_\epsilon$-benzyl-oxycarbonyl-S-lysyl-(2S,3aR,6aS)-octahydrocyclopenta[b]-pyrrole-2-carboxylate Tert.-butyl N-(1-S-carboethoxy-3-cyclohexylpropyl)-N$_\epsilon$-benzyloxycarbonyl-S-lysyl-(2S,3aR,6aS)-octahydrocyclopenta[b]pyrrole-2-carboxylate Benzyl N-(1-S-carboethoxy-3-phenylpropyl)-O-ethyl-S-tyrosyl-(2S,3aR,6aS)-octahydrocyclopenta[b]pyrrole-2-carboxylate Benzyl N-(1-S-carboethoxy-3-cyclopentylpropyl)-S-alanyl-2-(2S,3aR,6aS)-octahydrocyclopenta[b]pyrrole-2-carboxylate Benzyl N-(1-S-carboethoxy-3-phenylpropyl)-S-alanyl-S-2-azabicyclo[2.2.2]octane-3-carboxylate Benzyl N-(1-S-carboethoxy-3-phenylpropyl)-O-ethyl-S-tyrosyl-S-2-azabicyclo[2.2.2]octane-3-carboxylate Benzyl N-(1-S-carboethoxy-3-cyclohexylpropyl)-S-alanyl-S-2-azabicyclo[2.2.2]octane-3-carboxylate Tert.-butyl N-(1-S-carboethoxy-3-cyclohexylpropyl)-N$_\epsilon$-benzyloxycarbonyl-S-2-azabicyclo[2.2.2]octane-3-carboxylate Tert.-butyl N-(1-S-carboethoxy-3-phenylpropyl)-N$_\epsilon$-benzyloxycarbonyl-S-lysyl-S-2-azabicyclo[2.2.2]octane-3-carboxylate Benzyl N-(1-S-carboethoxy-3-cyclopentylpropyl)-S-alanyl-S-2-azabicyclo[2.2.2]octane-3-carboxylate Benzyl N-(1-S-carboethoxy-3-phenylpropyl)-S-alanyl-3S-exo-2-azabicyclo[2.2.1]heptane-3-carboxylate Benzyl N-(1-S-carboethoxy-3-cyclohexylpropyl)-S-alanyl-3S-exo-2-azabicyclo[2.2.1]heptane-3-carboxylate Tert.-butyl N-(1-S-carboethoxy-3-phenylpropyl)-N$_\epsilon$-benzyloxycarbonyl-S-lysyl-3-S-exo-2-azabicyclo[2.2.1]heptane-3-carboxylate Benzyl N-(1-S-carboethoxy-3-phenylpropyl)-S-alanyl-3S-endo-2-azabicyclo[2.2.1]heptane-3-carboxylate Benzyl N-(1-S-carboethoxy-3-cyclohexylpropyl)-S-alanyl-3S-endo-2-azabicyclo[2.2.1]heptane-3-carboxylate Tert.-butyl N-(1-S-carboethoxy-3-phenylpropyl)-N$_\epsilon$-benzyloxycarbonyl-S-lysyl-3-S-endo-2-azabicyclo[2.2.1]heptane-3-carboxylate Benzyl N-(1-S-carboethoxy-3-phenylpropyl)-O-ethyl-S-tyrosyl-3S-endo-2-azabicyclo[2.2.1]heptane-3-carboxylate Benzyl N-(1-S-carboethoxy-3-phenylpropyl)-S-alanyl-2-azaspiro[4.5]decane-3-S-carboxylate Benzyl N-(1-S-carboethoxy-3-phenylpropyl)-O-ethyl-S-tyrosyl-2-azaspiro[4.5]decane-3-S-carboxylate Tert.-butyl N-(1-S-carboethoxy-3-phenylpropyl)-N$_\epsilon$-benzyloxycarbonyl-S-lysyl-2-azaspiro[4.5]decane-3-S-carboxylate Benzyl N-(1-S-carboethoxy-3-cyclohexylpropyl)-S-alanyl-2-azaspiro[4.5]decane-3-S-carboxylate Tert.-butyl N-(1-S-carboethoxy-3-cyclohexylpropyl)-N$_\epsilon$-benzyloxycarbonyl-S-lysyl-2-azaspiro[4.5]decane-3-S-carboxylate Benzyl N-(1-S-carboethoxy-3-phenylpropyl)-S-alanyl-2-azaspiro[4.4]nonane-3-S-carboxylate Benzyl N-(1-S-carboethoxy-3-phenylpropyl)-O-ethyl-S-tyrosyl-2-azaspiro[4.4]nonane-3-S-carboxylate Benzyl N-(1-S-carboethoxy-3-phenylpropyl)-N$_\epsilon$-tert.-butoxycarbonyl-S-lysyl-2-azaspiro[4.4]nonane-3-S-carboxylate Benzyl N-(1-S-carboethoxy-3-cyclohexylpropyl)-S-alanyl-2-azaspiro[4.4]nonane-3-S-carboxylate Benzyl N-(1-S-carboethoxy-3-cyclopentylpropyl)-S-alanyl-2-azaspiro[4.4]nonane-3-S-carboxylate Benzyl N-(1-S-carboethoxy-3-cyclopentylpropyl)-N$_\epsilon$-tert.-butoxycarbonyl-S-lysyl-2-azaspiro[4.4]nonane-3-S-carboxylate Benzyl N-(1-S-carboethoxy-3-phenylpropyl)-S-alanyl-spiro-[bicyclo[2.2.1]heptane-2,3'-pyrrolidine]-5'-S-carboxylate Benzyl N-(1-S-carboethoxy-3-phenylpropyl)-O-ethyl-S-tyrosylspiro[bicyclo[2.2.1]heptane-2,3'-pyrrolidine]-5'-S-carboxylate Tert.-butyl N-(1-S-carboethoxy-3-phenylpropyl)-N$_\epsilon$-benzyloxycarbonyl-S-lysylspiro[bicyclo[2.2.1]heptane-2,3'-pyrrolidine]-5'-S-carboxylate Benzyl N-(1-S-carboethoxy-3-cyclohexylpropyl)-S-alanylspiro[bicyclo[2.2.1]heptane-2,3'-pyrrolidine]-5'-S-carboxylate Benzyl N-(1-S-carboethoxy-3-cyclohexylpropyl)-N$_\epsilon$-tert.-butoxycarbonyl-S-lysylspiro[bicyclo[2.2.1]heptane-2,3'-pyrrolidine]-5'-S-carboxylate Benzyl N-(1-S-carboethoxy-3-phenylpropyl)-S-alanylspiro[bicyclo[2.2.2]octane-2,3'-pyrrolidine]-5'-S-carboxylate Benzyl N-(1-S-carboethoxy-3-phenylpropyl)-O-ethyl-S-tyrosylspiro[bicyclo[2.2.2]octane-2,3'-pyrrolidine]-5'-carboxylate Benzyl N-(1-S-carboethoxy-3-phenylpropyl)-N$_\epsilon$-tert.-butoxycarbonyl-S-lysylspiro[bicyclo[2.2.2]octane-2,3'-pyrrolidine]-5'-S-carboxylate Benzyl N-(1-S-carboethoxy-3-cyclohexylpropyl)-S-alanylspiro[bicyclo[2.2.2]octane-2,3'-pyrrolidine]-5'-S-carboxylate Benzyl N-(1-S-carboethoxy-3-phenylpropyl)-S-alanylazatricyclo[4.3.0.1$^{6,9}$]decane-3-S-carboxylate Benzyl N-(1-S-carboethoxy-3-phenylpropyl)-O-ethyl-S-tyrosyl-2-azatricyclo[4.3.0.1$^{6,9}$]decane-3-S-carboxylate Tert.-butyl N-(1-S-carboethoxy-3-phenylpropyl)-N$_\epsilon$-benzyloxycarbonyl-S-lysyl-2-azatricyclo[4.3.0.1$^{6,9}$]-decane-3-S-carboxylate Benzyl N-(1-S-carboethoxy-3-cyclohexylpropyl)-S-alanyl-2-azatricyclo[4.3.0.1$^{6,9}$]decane-3-S-carboxylate Tert.-butyl N-(1-S-carboethoxy-3-phenylpropyl)-N$_\epsilon$-benzyloxycarbonyl-S-lysyl-2-azatricyclo[4.3.0.1$^{6,9}$]-decane-3-S-carboxylate Benzyl N-(1-S-carboethoxy-3-phenylpropyl)-S-alanyl-decahydrocyclohepta[b]pyrrole-2-S-carboxylate Benzyl N-(1-S-carboethoxy-3-phenylpropyl)-O-ethyl-S-tyrosyldecahydrocyclohepta[b]pyrrole-2-S-carboxylate Tert.-butyl N-(1-S-carboethoxy-3-phenylpropyl)-N$_\epsilon$-benzyloxycarbonyl-S-lysyldecahydrocyclohepta[b]pyrrole-2-S-carboxylate Benzyl N-(1-S-carboethoxy-3-cyclohexylpropyl)-S-alanyldecahydrocyclohepta[b]pyrrole-2-S-carboxylate Benzyl N-(1-S-carboethoxy-3-cyclohexylpropyl)-N$_\epsilon$-tert.-butoxycarbonyl-S-lysyldecahydrocyclohepta[b]pyrrole-2-S-carboxylate Benzyl N-(1-S-carboethoxy-3-phenylpropyl)-S-alanyl-transoctahydroisoindole-1-S-carboxylate Benzyl N-(1-S-carboethoxy-3-phenylpropyl)-S-alanyl-cis-octahydroisoindole-1-S-carboxylate Benzyl N-(1-S-carboethoxy-3-cyclohexylpropyl)-S-alanyl-trans-octahydroisoindole-1-S-carboxylate Benzyl N-(1-S-carboethoxy-3-cyclohexylpropyl)-S-alanyl-cis-octahydroisoindole-1-S-carboxylate Benzyl N-(1-S-carboethoxy-3-phenylpropyl)-S-alanyl-cis-octahydrocyclopenta[c]pyrrole-1-S-carboxylate Benzyl N-(1-S-carboethoxy-3-cyclohexylpropyl)-S-alanyl-cis-octahydrocyclopenta[c]pyrrole-1-S-carboxylate Benzyl N-(1-S-carboethoxy-3-cyclohexylpropyl)-$N_\epsilon$-tert.-butoxycarbonyl-S-lysyl-cis-octahydrocyclopenta[c]pyrrole-1-S-carboxylate Tert.-butyl N-(1-S-carboethoxy-3-phenylpropyl)-S-alanyl-2,3,3a,4,5,7a-hexahydroindole-cis,endo-2-S-carboxylate Tert.-butyl N-(1-S-carboethoxy-3-cyclohexylpropyl)-O-ethyl-S-tyrosyl-2,3,3a,4,5,7a-hexhydroindole-2-S-carboxylate Tert.-butyl N-(1-S-carboethoxy-3-cyclohexylpropyl)-S-alanyl-2,3,3a,4,5,7a-hexahydroindole-2-S-carboxylate Tert.-butyl N-(1-S-carboethoxy-3-phenylpropyl)-S-alanylthiazolidine-5-S-carboxylate Tert.-butyl N-(1-S-carboethoxy-3-cyclohexylpropyl)-S-alanylthiazolidine-5-S-carboxylate Tert.-butyl N-(1-S-carboethoxy-3-phenylpropyl)-$N_\epsilon$-benzyloxycarbonyllysylthiazolidine-5-S-carboxylate Tert.-butyl N-(1-S-carboethoxy-3-cyclohexylpropyl)-$N_\epsilon$-benzyloxycarbonyl-S-2-azabicyclo[3.1.0]hexane-3-carboxylate Tert.-butyl N-(1-S-carboethoxy-3-phenylpropyl)-$N_\epsilon$-benzyloxycarbonyl-S-lysyl-S-2-azabicyclo[3.1.0]hexane-3-carboxylate and Benzyl N-(1-S-carboethoxy-3-cyclopentylpropyl)-S-alanyl-S-2-azabicyclo[3.1.0]hexane-3-carboxylate.

The reaction according to the invention is preferably carried out in a neutral or weakly alkaline medium. It is most straightforward to adjust the pH of the medium by adding aliphatic or cycloaliphatic tertiary bases, such as N-methylmorpholine, N-ethylmorpholine, or trialkylamines having up to 6 carbon atoms per alkyl radical. Moreover, when carried out, as preferred, in two-phase aqueous systems, it is possible to use, in place of the organic base, alkaline salts acting as buffer systems, for example salts of carbonic acid or of phosphoric acid.

All inert solvents customary in peptide synthesis can be used as solvents, for example methylene chloride, ethyl acetate, chloroform, dimethylformamide, dimethylacetamide, dioxane or tetrahydrofuran.

It is also possible to carry out the synthesis in mixed aqueous solvent systems. These are understood to include mixtures of water and an organic solvent which is miscible with water, such as dioxane/water, tetrahydrofuran/water or dimethylformamide/water. Surprisingly, two-phase systems, such as $CH_2Cl_2$/water, ethyl acetate/water or 3-methyltetrahydropyran/water, with $Na_2CO_3$ or $K_2CO_3$ as the base, are particularly suitable (thorough stirring is necessary).

As a rule, the rate of the reaction at room temperature is satisfactory. Gentle warming has no adverse effects. Higher temperatures, above about 50° C., are not advisable because of the danger or racemization, and they are unnecessary.

The phosphinic anhydrides according to the invention are preferably employed in excess (about 1.2–2.5 mol of phosphinic anhydride per mol of bond to be formed). They can be added dropwise to the reaction mixture in the undiluted form or dissolved in the organic solvent.

Ethylmethylphosphinic anhydride is particularly suitable, since it is soluble both in water and in organic solvents, and the mixed anhydrides formed from it and carboxylic acids have the desired moderate activity at room temperature. This compound can be employed particularly advantageously in a "one pot process", since no reaction whatever of the anhydride with amino groups has been observed. The mixed anhydride VI, which is formed from II in situ in the presence of bases, reacts exclusively and in virtually quantitative yield with the amino acid esters of the formula IV.

The moderate activity of the mixed anhydride has the additional advantageous effect in industrial batches that only a small quantity of heat is evolved and cooling problems do not arise.

A particularly advantageous variant of the process results from the fact that the reaction can be carried out in two phases, in water and a solvent which is immiscible or miscible to only a limited extent with water, such as, for example, $CH_2Cl_2$ or AcOEt, and in which the reaction product (I) is soluble but the starting materials and other reagents which have been added (salts of tertiary organic bases, sodium carbonate, salts of phosphinic acid and the like) are only sparingly soluble.

The reaction takes place without racemization ($<2\%$) and there is no interference from water contained in solvents and reagents, indeed it is even possible to carry it out particularly advantageously in water or two-phase systems using organic (NEM, $Et_3N$ etc.) or, preferably, inorganic bases (for example sodium carbonate).

When using an organic or mixed organic medium, it is possible, after reaction is complete, to remove most starting materials and impurities from the organic phase by extraction by shaking with aqueous $KHSO_4/K_2SO_4$ solution (pH2) and then with sodium carbonate/bicarbonate solution. After evaporation of the organic phase, the resulting products remain as oils and these are converted into biologically active substances by, for example, hydrogenation (for example in the case where $R^3$ is benzyl or nitrobenzyl) or acid treatment (for example when $R^3$ is $Bu^t$).

The compounds of the formula I are inhibitors of angiotensin converting enzyme (ACE) or are intermediates in the preparation of inhibitors of this type, and they can be employed to control high blood pressure of a variety of etiologies. Compounds of this type are known from, for example, U.S. Pat. Nos. 4,344,949, 4,374,847, 4,350,704, European Patent A 50,800, European Patent A 31,741, European Patent A 51,020, European Patent A 49,658, European Patent A 49,605, European Patent A 29,488, European Patent A 46,953 and European Patent A 52,870. The following German Patent Applications also relate to them: P 3,226,768.1, P 3,151,690.4, P 3,210,496.0, P 3,211,397.8, P 3,211,676.4, P 3,227,055.0, P 3,242,151.6, P 3,246,503.3 and P 3,246,757.5.

The examples which follow are intended to illustrate the process according to the invention without restricting the invention to the substances which are mentioned here as being representative.

EXAMPLE 1

Homogeneous Process 85 g of benzyl S,S,S-azabicyclo[3.3.0]octane-3-carboxylate hydrochloride and 88 g of (S,N-(1-carboethoxy-3-phenylpropyl)alanine are suspended in 500 ml of methylene chloride. 120 ml of ethylmethylphosphinic anhydride (in the form of a 50% strength solution in methylene chloride) and 200 ml of triethylamine are added, with stirring, within 1 hour. The extent of conversion is checked after 2 hours using thin-layer chromatography (silica gel system: CHCl₃/MeOH-/AcOH 50+10+3). If the benzyl ester of the amino acid is still detectable, a further 20 ml of anhydride and 50 ml of Et₃N are added. The mixture is left at room temperature for some hours (overnight if necessary), and the reaction mixture is evaporated in vacuo, diluted with methylene chloride (500 ml) to a total volume of about 1 liter and this is extracted with 1×500 ml of potassium bisulfate/potassium sulfate solution (50 g of KHSO₄ in 1 liter of water), and with 2×500 ml each time of an aqueous 5% NaHCO₃ solution. The organic phase is dried over some solid sodium sulfate and filtered through a layer of silica gel 2-3 cm thick. This is washed with 250 ml of methylene chloride or ethyl acetate and the almost colorless eluate is evaporated. Yield: 85-95% of theory. To check the yield and purity of the product, it is possible to remove the benzyl group catalytically by the process described (methanol/Pd/C). The reaction product ((S)-N-(1-carboethoxy-3-phenylpropyl)alanyl-2-azabicyclo[3.3.0]octane-3-carboxylic acid) crystallizes from ether in a yield of 80-90% (based on benzyl (S)-azabicyclo[3.3.0]octane-3-carboxylate hydrochloride).

Melting point: 109° C.; [α]$_D^{24}$ = +15.8° (C=1, methanol).

EXAMPLE 2

Two-Phase Process 28.2 g of benzyl (S,S,S)-azabicyclo[3.3.0]octane-3-carboxylate.HCl and 29.5 g of (S)-N-(carboethoxy-3-phenyl-1-propyl)alanine are suspended in a mixture of 150 ml of water and 100 ml of methylene chloride. While stirring vigorously, a solution of 70 g of potassium carbonate (or an equivalent amount of sodium carbonate) in 150 ml of water and, at the same time, about 150 ml of a 25% strength solution of methylethylphosphinic anhydride in methylene chloride, or a corresponding amount of MEPA at another concentration, are slowly added. The pH should be between 9 and 10; addition is complete in about 2 hours. After a further 2 hours, completion of the reaction is checked by the absence of the benzyl ester of the amino acid in the organic phase on thin-layer chromatography. The mixture is diluted with a further 250 ml of methylene chloride, and the aqueous phase is separated off.

The organic phase is extracted with 1×100 ml of an aqueous solution of 50 g of KHSO₄ and 100 g K₂SO₄ per liter, and then with 1×250 ml of a 5% strength aqueous solution of NaHCO₃/Na₂CO₃. The organic phase is dried over 10 g of solid sodium sulfate and then evaporated in vacuo. The remaining colorless oil can be further processed as indicated in Example 1. Yield of crystalline final product: 80-90%. The physical data of the final product obtained in this manner are consistent with those for the product obtained in Example 1, and the former is distinguished by a particularly high purity. (TLC: ready-coated silica gel plates (MERCK AG) SiO₂-60; system CHCl₃/MeOH/HOAc 50:10:5 (V:V)).

The addition of the base can also be carried out using an autotitrator at a constant pH.

EXAMPLE 3

Two-Phase Process 29.0 g of benzyl [S.S.S]-octahydroindole-2-carboxylate.HCl and 29.5 g of (S)-N-3-phenyl-1-carboethoxypropylalanine are suspended in a mixture of 200 ml of water and 100 ml of methylene chloride. While stirring vigorously, a solution of 70 g of potassium carbonate (or an equivalent amount of sodium carbonate) in 150 ml of water and, at the same time, 150 ml of a 25% strength solution of methylethylphosphinic anhydride in methylene chloride are added slowly. The pH should be between 9 and 10; when 3-methyltetrahydropyran is used as the organic solvent, the process can be carried out at pH 7-9. Addition is complete in about 2 hours. After a further 2 hours, completion of reaction is checked by the absence of the benzyl ester of the amino acid in the organic phase on thin-layer chromatography. The mixture is diluted with a further 250 ml of methylene chloride, and the aqueous phase is separated off.

The organic phase is extracted with 1×100 ml of an aqueous solution of 50 g of KHSO₄ and 100 g of K₂SO₄ per liter and then with 1×250 ml of a 5% strength aqueous solution of NaHCO₃/Na₂CO₃. The organic phase is dried over 10 g of solid sodium sulfate and it is then evaporated in vacuo. The remaining colorless oil can be further processed in analogy to Example 1.

The product thus obtained is converted with HCl into crystalline[S,S,S,S,S]-N-[(1-carboethoxy-3-phenylpropyl)alanyl]octahydroindole-2-carboxylic acid hydrochloride, the physical data of which are consistent with those known from the literature.

We claim:

1. A process for the preparation of a compound of the formula I

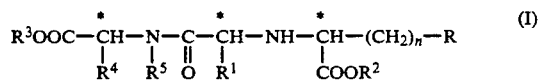

in which n is 1 or 2;

R denotes hydrogen,
  an optionally substituted aliphatic radical having 1 to 8 carbon atoms,
  an optionally substituted alicyclic radical having 3-9 carbon atoms,
  an optionally substituted aromatic radical having 6-12 carbon atoms,
  an optionally substituted araliphatic radical having 7-14 carbon atoms,
  an optionally substituted alicyclic-aliphatic radical having 7-14 carbon atoms, or
  a radical OR$^a$ or SR$^a$, in which R$^a$ represents an optionally substituted aliphatic radical having 1-4 carbon atoms, an optionally substituted aromatic radical having 6-12 carbon atoms or an optionally substituted heteroaromatic radical having 5-12 ring atoms;

R$^1$ denotes hydrogen,
  an optionally substituted aliphatic radical having 1-6 carbon atoms,
  an optionally substituted alicyclic radical having 3-9 carbon atoms,
  an optionally substituted alicyclic-aliphatic radical having 4-13 carbon atoms,
  an optionally substituted aromatic radical having 6-12 carbon atoms,
  an optionally substituted araliphatic radical having 7-16 carbon atoms,
  an optionally substituted heteroaromatic radical having 5-12 ring atoms, or if not already included above, the side chain, protected when appropriate, of a naturally occurring alpha-amino acid;

R$^2$ and R$^3$ are identical or different and denote hydrogen,
an optionally substituted aliphatic radical having 1-6 carbon atoms,
an optionally substituted alicyclic radical having 3-9 carbon atoms,
an optionally substituted aromatic radical having 6-12 carbon atoms, or
an optionally substituted araliphatic radical having 7-16 carbon atoms; and R$^4$ and R$^5$, together with the atoms bearing them, form an optionally substituted octahydrocyclopenta[b]pyrrole ring system;

which process comprises reacting a compound of the formula II

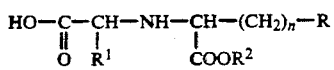  (II)

in which n, R, R$^1$ and R$^2$ have the meanings defined above, and where the amine group —NH— shown in the structure of the compound of formula II is unprotected, in the presence of at least one phosphinic anhydride of the formula III

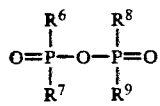  (III)

in which R$^6$, R$^7$, R$^8$ and R$^9$ are identical or different and represent alkyl and/or aralkyl, with a compound of the formula IV

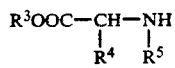  (IV)

in which R$^3$, R$^4$ and R$^5$ have the meanings defined above.

2. The process as claimed in claim 1, wherein benzyl[S,S,S,S,S]-N-(1-carboethoxy-3-phenylpropyl)-alanyl-octahydrocyclopenta[b]pyrrole-2-carboxylate is prepared.

3. The process as claimed in claim 1, wherein is prepared a compound of the formula I in which n is 1 or 2, R denotes hydrogen, alkyl having 1-8 carbon atoms, alkenyl having 2-6 carbon atoms, cycloalkyl having 3-9 carbon atoms, aryl having 6-12 carbon atoms, which can be monosubstituted disubstituted or trisubstituted by $(C_1-C_4)$-alkyl, $(C_1-C_4)$-alkoxy, hydroxyl, halogen, nitro, amino, aminomethyl, $(C_1-C_4)$-alkylamino, di-$(C_1-C_4)$-alkylamino $(C_1-C_4)$-acylamino, methylenedioxy, carboxyl, cyano and/or sulfamoyl, alkoxy having 1-4 carbon atoms, aryloxy having 6-12 carbon atoms, which can be substituted as described above for aryl, monocyclic or bicyclic heteroaryloxy having 5-7 or 8-10 ring atoms respectively, 1 or 2 of these ring atoms being sulfur or oxygen atoms and/or 1 to 4 ring atoms being nitrogen, which can be substituted as described above for aryl, amino-$(C_1-C_4)$-alkyl, $(C_1-C_4)$-alkanoylamino-$(C_1-C_4)$-alkyl, $(C_7-C_{13})$-aroylamino-$(C_1-C_4)$-alkyl, $(C_1-C_4)$-alkoxycarbonylamino-$(C_1-C_4)$-alkyl, $(C_6-C_{12})$-aryl-$(C_1-C_4)$-alkoxycarbonylamino-$(C_1-C_4)$-alkyl, $(C_6-C_{12})$-aryl-$(C_1-C_4)$-alkylamino-$(C_1-C_4)$-alkyl, $(C_1-C_4)$-alkylamino-$(C_1-C_4)$-alkyl, di-$(C_1-C_4)$-alkylamino $(C_1-C_4)$-alkyl, guanidino-$(C_1-C_4)$-alkyl, imidazolyl, indolyl, $(C_1-C_4)$-alkylthio, $(C_1-C_4)$-alkylthio-$(C_1-C_4)$-alkyl, $(C_6-C_{12})$-arylthio-$(C_1-C_4)$-alkyl, which can be substituted in the aryl moiety as described above for aryl, $(C_6-C_{12})$-aryl-$(C_1-C_4)$-alkylthio, which can be substituted in the aryl moiety as described above for aryl, carboxy-$(C_1-C_4)$-alkyl, carboxyl, carbamoyl, carbamoyl-$(C_1-C_4)$-alkyl, $(C_1-C_4)$-alkoxycarbonyl-$(C_1-C_4)$-alkyl, $(C_6-C_{12})$-aryloxy-$(C_1-C_4)$-alkyl, which can be substituted in the aryl moiety as described above for aryl, or $(C_6-C_{12})$-aryl-$(C_1-C_4)$-alkoxy, which can be substituted in the aryl moiety as described above for aryl, R$^1$ denotes hydrogen, alkyl having 1-6 carbon atoms, alkenyl having 2-6 carbon atoms, alkynyl having 2-6 carbon atoms, cycloalkyl having 3-9 carbon atoms, cycloalkenyl having 5-9 carbon atoms, $(C_3-C_9)$-cycloalkyl-$(C_1-C_4)$-alkyl, $(C_5-C_9)$-cycloalkenyl-$(C_1-C_4)$-alkyl, optionally partially hydrogenated aryl having 6-12 carbon atoms, which can be substituted as described above for R, $(C_6-C_{12})$-aryl-$(C_1-C_4)$-alkyl or $(C_7-C_{13})$-aroyl-$(C_1$ or $C_2)$-alkyl, both of which can be substituted as the previous aryl, monocyclic or bicyclic, optionally partially hydrogenated, heteroaryl having 5-7 or 8-10 ring atoms respectively, 1 or 2 of these ring atoms being sulfur or oxygen atoms and/or 1 to 4 ring atoms being nitrogen atoms, which can be substituted as the previous aryl, or the optionally protected side chain of a naturally occurring alpha-amino acid R$^1$—CH(NH$_2$)—COOH, R$^2$ and R$^3$ are identical or different and denote hydrogen, alkyl having 1-6 carbon atoms, alkenyl having 2-6 carbon atoms, di-$(C_1-C_4)$-alkylamino-$(C_1-C_4)$-alkyl, $(C_1-C_5)$-alkanoyloxy-$(C_1-C_4)$-alkyl, $(C_1-C_6)$-alkoxycarbonyloxy-$(C_1-C_4)$-alkyl, $(C_7-C_{13})$-aroyloxy-$(C_1-C_4)$-alkyl, $(C_6-C_{12})$-aryloxycarbonyloxy-$(C_1-C_4)$-alkyl, aryl having 6-12 carbon atoms, $(C_6-C_{12})$-aryl-$(C_1-C_4)$-alkyl, $(C_3-C_9)$-cycloalkyl or $(C_3-C_9)$ cycloalkyl-$(C_1-C_4)$-alkyl, and R$^4$ and R$^5$ are as defined in claim 16, where during the reaction the free amino, alkylamino, hydroxyl, carboxyl, mercapto and/or guanidino groups present, where appropriate, are protected in the radicals R to R$^5$.

4. The process as claimed in claim 1, which is carried out in the presence of ethylmethylphosphinic anhydride.

5. The process as claimed in claim 1, wherein the reaction is carried out in an inert organic solvent in the presence of a tertiary organic amine.

6. The process as claimed in claim 4, wherein the reaction with ethylmethylphosphinic anhydride is carried out in two phases using an aqueous inorganic base (at pH 7-10) and an organic solvent which is immiscible, or only miscible to a limited extent, with water.

7. The process as claimed in claim 1, wherein tert.-butyl (S,S,S,S,S)-N-(1-carboethoxy-3-phenylpropyl)-alanyl-octahydrocyclopenta[b]pyrrole-2-carboxylate is prepared.

8. The process as claimed in claim 1, wherein the reaction is carried out in two phases using an aqueous inorganic base and an organic solvent which is immiscible, or miscible to only a limited extent, with water, the addition of base being carried out using a pH-controlled autotitrator.

9. The process as claimed in claim 6, wherein said organic solvent is selected from the group consisting of methylene chloride, ethyl acetate and 3-methyltetrahydropyran.

10. The process as claimed in claim 1, wherein said process is conducted under mild conditions.

11. The process as claimed in claim 1, wherein said process is carried out in a neutral or weakly alkaline medium.

12. The process as claimed in claim 11, wherein an aliphatic or cycloaliphatic tertiary base is added.

13. The process as claimed in claim 3, wherein, in the definition of R, said $(C_1-C_4)$-acylamino substituent is $(C_1-C_4)$-alkanoylamino.

14. The process as claimed in claim 1, wherein methylene chloride is employed as a solvent.

15. The process as claimed in claim 1, wherein a lower alkyl acetate is employed as a solvent.

16. The process as claimed in claim 1, wherein said process is carried out in a mixture of water and an organic solvent.

17. The process as claimed in claim 1, further comprising the step(s) of eliminating radicals which have been introduced to protect one or more functional groups and/or esterifying free carboxyl groups.

18. The process as claimed in claim 15, wherein said lower alkyl acetate is ethyl acetate.

* * * * *

UNITED STATES PATENT AND TRADEMARK OFFICE
CERTIFICATE OF CORRECTION

PATENT NO. : 5,068,351

DATED : November 26, 1991

INVENTOR(S) : Volker Teetz, et. al.

It is certified that error appears in the above-indentified patent and that said Letters Patent is hereby corrected as shown below:

On the Title page, item [54] and col. 1, line 3, "(6) should read (B).
Column 15, line 56, after "$(C_1-C_4)$ -alkylamino" insert --,--.
Column 16, line 41, "in claim 16" should read --in claim 1--.

Signed and Sealed this

Fifteenth Day of June, 1993

Attest:

MICHAEL K. KIRK

Attesting Officer

Acting Commissioner of Patents and Trademarks